United States Patent
Qin et al.

(10) Patent No.: US 9,505,623 B1
(45) Date of Patent: Nov. 29, 2016

(54) ONE-STEP SYNTHESIS OF GRAPHENE QUANTUM DOTS

(71) Applicants: Yiru Qin, Tampa, FL (US); Shu-Feng Zhou, Tampa, FL (US)

(72) Inventors: Yiru Qin, Tampa, FL (US); Shu-Feng Zhou, Tampa, FL (US)

(73) Assignee: University of South Florida, Tampa, FL (US)

( * ) Notice: Subject to any disclaimer, the term of this patent is extended or adjusted under 35 U.S.C. 154(b) by 17 days.

(21) Appl. No.: 14/747,332

(22) Filed: Jun. 23, 2015

Related U.S. Application Data

(60) Provisional application No. 62/016,321, filed on Jun. 24, 2014.

(51) Int. Cl.
| | | |
|---|---|---|
| *C01B 31/04* | (2006.01) | |
| *C09K 11/65* | (2006.01) | |
| *B82Y 20/00* | (2011.01) | |
| *B82Y 40/00* | (2011.01) | |
| *B82Y 5/00* | (2011.01) | |

(52) U.S. Cl.
CPC ........... *C01B 31/0446* (2013.01); *C09K 11/65* (2013.01); *B82Y 5/00* (2013.01); *B82Y 20/00* (2013.01); *B82Y 40/00* (2013.01); *C01B 2204/32* (2013.01); *Y10S 977/774* (2013.01)

(58) Field of Classification Search
CPC .......... C01B 31/0446; C01B 2204/32; C09K 11/65; B82Y 5/00; B82Y 20/00; B82Y 40/00; Y10S 977/774
USPC ........................................................ 423/448
See application file for complete search history.

(56) References Cited

U.S. PATENT DOCUMENTS

| | | | |
|---|---|---|---|
| 8,664,637 B2 | 3/2014 | Jang et al. | |
| 2012/0272868 A1* | 11/2012 | Berry ..................... | B82Y 30/00 106/286.8 |

FOREIGN PATENT DOCUMENTS

| | | | |
|---|---|---|---|
| CN | 103265020 A | 8/2013 | |
| CN | 103432590 A | 12/2013 | |

OTHER PUBLICATIONS

Dong, et al., One-step and high yield simultaneous preparation of single- and multi-layer graphene quantum dots from CX-72 carbon black, J. Mater. Chem. 2012; 22: 8764.*
Minghan Xu et al., "Hydrothermal/Solvothermal Synthesis of Graphene Quantum Dots and Their Biological Applications", Nano Biomed Eng., 5.2:65-71 (2013).
Dengyu Pan et al., "Hydrothermal Route for Cutting Graphene Sheets into Blue-Luminescent Graphene Quantum Dots", Advanced Materials, 22.6:734-738 (2010).
Yonghun Shin et al., "Mass Production of Graphene Quantum Dots by One-Pot Synthesis Directly from Graphite in High Yield", Small, 10.5:866-870 (2014).
Mei-Ling Chen, et al. "Quantum-Dot-Conjugated Graphene as a Probe for Simultaneous Cancer-Targeted Fluorescent Imaging, Tracking, and Monitoring Drug Delivery", Bioconjugate Chemistry, 24, 387-397 (2013).
Abdullah-Al-Nahain, et al. "Target Delivery and Cell Imaging Using Hyaluronic Acid-Functionalized Graphene Quantum Dots", Mol. Pharmaceutics, 10, 3736-3744 (2013).
Israa Al-Ogaidi, et al. "Detection of the Ovarian Cancer Biomarker CA-125 Using Chemiluminescence Resonance Energy Transfer to Graphene Quantum Dots", Chem. Commun., 50, 1344-1346 (2014).
Preeti Nigam, et al. "Graphene Quantum Dots Conjugated Albumin Nanoparticles for Targeted Drug Delivery and Imaging of Pancreatic Cancer", J. Mater. Chem. B., 2, 3190-3195 (2014).

* cited by examiner

*Primary Examiner* — Daniel C McCracken
(74) *Attorney, Agent, or Firm* — Thomas | Horstemeyer, LLP

(57) ABSTRACT

Methods of making graphene quantums dots are provided. The methods can produce graphene quantum dots with a monodisperse size distribution. The graphene quantum dots are produced, via one-pot synthesis, from a graphene source and a strong oxidizing mixture at an elevated temperature. The strong oxidizing mixture can contain one or more permanganates and one or more oxidizing acids. Exemplary permanganates include sodium permanganate, potassium permanganate, and calcium permanganate. Exemplary oxidizing acids include nitric acid and sulfuric acid. The graphene quantum dots can have an average particle size of between about 1 nm and 20 nm and a monodisperse size distribution. For example, the size distribution can have a span about 1 or less and/or a coefficient of variance of about 0.5 or less. About 40% or more of the graphene quantum dots can have a diameter within ±5 nm of the average particle size of the graphene quantum dots.

25 Claims, 9 Drawing Sheets

ONE-STEP SYNTHESIS OF GRAPHENE QUANTUM DOTS

CROSS-REFERENCE TO RELATED APPLICATIONS

This application claims priority to U.S. Ser. No. 62/016,231 filed Jun. 24, 2014.

BACKGROUND

Graphene and graphene quantum dots have seen numerous applications as useful materials, including applications in optics, electronics, and biomedical applications. Graphene, a typical $sp^2$ carbon-based material, has attracted tremendous interests after its first being isolated in 2004. Graphene oxides and graphene quantum dots have excellent physical and chemical properties, graphene and its derivatives, such as graphene oxide (GO) and graphene quantum dots (GQDs), have exhibited great potential in optical, electrochemical, and biomedical applications. Among them, biomedical applications of GQDs represent a relatively new but fast growing area, for example, bioimaging, biosensor materials, and drug delivery. By combining the advantages of graphene and quantum dots (QDs), these graphene quantum dots are expected to be a promising therapeutic and diagnostic tool for various diseases.

Although several methods have been developed for the synthesis of graphene quantum dots, there are still many deficiencies in those methods such as the need for high energy or radiation times. The starting material of those methods is graphene oxide which needs to be synthesized from graphite first and those methods take long time and multiple steps to obtain graphene quantum dots with low yield. Methods of preparing quantum dots have been attempted using vapor deposition processes, such as MOCVD (Metal Organic Chemical Vapor Deposition) or MBE (Molecular Beam Epitaxy). Chinese Application No. 2013-10200476 described methods of making graphene quantum dots by first grinding a flake graphite to produce graphite nanoparticles, oxidizing the graphite nanoparticles with nitric acid at low temperature for 20 hours, dried, and then heated to 450° C. Furthermore, the methods described previously do not produce graphene quantum dots with high yields and with monodisperse and narrow size distributions.

Therefore, there remains a need for improved methods of making graphene quantum dots, especially small graphene quantum dots with monodisperse size distributions.

SUMMARY

Methods of making graphene quantum dots (GQDs) are provided. The methods include combining a graphene source with a strong oxidizing mixture to form a combination; and heating the combination to an elevated temperature to produce the GQDs. The graphene source can be carbon black, graphite, or a combination thereof. The elevated temperature can be about 100° C. or more about 100° C. to 200° C. or about 120° C. to 180° C. In some embodiments the heating is for a period of time of about 2 hours or less.

The oxidizing mixture can include oxidizing agents such as permanganates, hexafluoromanganates, persulfates, chromates, Fenton's reagent, oxidizing acids, and combinations thereof. The permanganates can include sodium permanganate, potassium permanganate, or calcium permanganate. The persulfates can include sodium peroxomonosulfate, sodium persulfate, potassium peroxymonosulfate, or ammonium persulfate. Oxidizing acids can include nitric acid, perchloric acid, chloric acid, chromic acid, sulfuric acid, and combinations thereof. In some embodiments the oxidizing mixture contains three or more oxidizing agents. In some embodiments the oxidizing mixture contains at least two oxidizing acids. In preferred embodiments the oxidizing mixture contains potassium permanganate, nitric acid, and sulfuric acid. The strong oxidizing mixture can contain one or more oxidizing agents having a standard electrode potential between 1.0 V and 2.5 V.

The methods can make small GQDs with a monodisperse size distribution. The GQDs can have an average diameter of between 1.0 and 20.0 nm, between 2.0 and 10.0 nm, or between 2.0 and 5.0 nm. The monodisperse size distribution can have a span of about 1 or less. The monodisperse size distribution can have a coefficient of variation of about 0.5 or less. In some embodiments, about 40% or more, preferably about 50% or more, of the GQDs have a diameter within ±0.5 nm of the average diameter of the GQDs.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
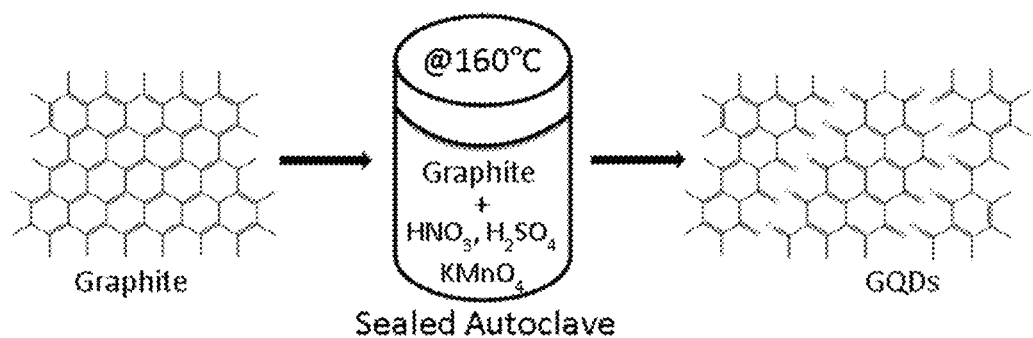
FIG. 1 is a schematic of one embodiment of a method of making graphene quantum dots. Graphite is combined with an oxidizing mixture of $HNO_3$, $H_2SO_4$, and $KMnO_4$ in a sealed autoclave and heated to 160° C. to produce graphene quantum dots having a monodisperse size distribution.

Graphene quantum dots (GQDs) and methods of making GQDs are provided. The methods can include combining a graphene source with a strong oxidizing mixture and heating to make the GQDs. The GQDs can be highly nanocrystaline with a monodipserse size distribution and an average diameter of about 10 nm, 7 nm, about 6 nm, about 5 nm, about 4 nm, about 3 nm, or less.

Before the present disclosure is described in greater detail, it is to be understood this disclosure is not limited to particular embodiments described, and may vary. It is also to be understood that the terminology used is to describe particular embodiments only, and is not intended to be limiting. The skilled artisan will recognize many variants and adaptations of the embodiments described. These variants and adaptations are included in the teachings of this disclosure and to be encompassed by the claims.

All publications and patents cited in this specification are incorporated by reference as if each individual publication or patent were specifically and individually indicated to be incorporated by reference and are incorporated by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could differ from the actual publication dates that may need to be independently confirmed.

Although any methods and materials similar or equivalent to those described can also be used in the practice or testing of the present disclosure, the preferred methods and materials are now described. Functions or constructions well-known in the art may not be described for brevity and/or clarity. Embodiments of the present disclosure will employ, unless otherwise indicated, techniques of nanotechnology, organic chemistry, material science and engineering which are within the skill of the art. Such techniques are explained fully in the literature.

Ratios, concentrations, amounts, and other numerical data can be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' and the range greater than 'x' and less than 'y'. The range can also be expressed as an upper limit, e.g. 'about x, y, z, or less' and should be interpreted to include the ranges of 'about x', 'about y', and 'about z' and the ranges of 'less than x', less than y', and 'less than z'. Likewise, the phrase 'about x, y, z, or greater' should be interpreted to include the ranges of 'about x', 'about y', and 'about z' and the ranges of 'greater than x', greater than y', and 'greater than z'. In some embodiments, the term "about" can include traditional rounding according to significant figures of the numerical value. In addition, the phrase "about 'x' to 'y'" includes "about 'x' to about 'y'".

DEFINITIONS

Unless defined otherwise, all technical and scientific terms used have the same meaning as commonly understood by one of ordinary skill in the art to which this disclosure belongs. It will be further understood that terms, such as those defined in commonly used dictionaries, should be interpreted as having a meaning consistent with their meaning in the specification and relevant art and should not be interpreted in an idealized or overly formal sense unless defined.

As used herein, the term "graphene quantum dot" or "GQD" refers to a nanocrystalline graphene material in which excitons are confined in all three spatial dimensions, as distinguished from quantum wires (quantum confinement in only two dimensions), quantum wells (quantum confinement in only one dimension), and bulk semiconductors (unconfined). Graphene quantum dots can contain from about 1 to 10, about 1 to 5, about 1 to 4, or about 1 to 3 layers of small pieces of graphene sheets, the edges of which may contain chemical defects such as from oxidation of the graphene. Also, many optical, electrical and chemical properties of the graphene quantum dot may depend on its size, and hence such properties may be modified or tuned by controlling its size. A graphene quantum dot may be a particle, the shape of which may be spheroidal, ellipsoidal, or other shape. The "size" of the graphene quantum dot may refer to a dimension characteristic of its shape or an approximation of its shape, and may be a diameter, a major axis, a predominant length, etc. The size of a graphene quantum dot is on the order of nanometers, i.e., about 1 nm to 1000 nm, but more typically about 1 nm to 100 nm, about 1 nm to 30 nm, about 1 nm to 20 nm, about 1 nm to 10 nm, or about 1 nm to 5 nm. In a plurality or ensemble of graphene quantum dots, the graphene quantum dots may be characterized as having an average size. The size distribution of a plurality of graphene quantum dots may be monodisperse. Graphene quantum dots are described in Sun et al., *Materials Today*, 2013, 16(11):433-442.

The term "graphene", as used herein, refers to two dimensional sheet of hexagonal carbon that includes single-layer graphene and few-layer graphene. The term "few-layer" graphene includes graphene having about 2-10 layers, preferably about 3-7 layers. The term "exfoliated graphite" includes about 11 layers of hexagonal carbon, or more. For example, exfoliated graphite can include about 11 layers of more of graphene that has been intercalated and subsequently removed from bulk graphite. The term "exfoliate," as used herein, refers to an expansion of a bulk graphite lattice. The term "graphite" includes intercalated graphite, exfoliated graphite, and in some aspects, graphene.

The term "carbon black", as used herein, refers to the materials commonly referred to as carbon black and includes cetylene black, channel black, furnace black, lamp black and thermal black. Carbon black can be produced, for example, by the incomplete combustion of heavy petroleum products.

The term "particle size" and "particle diameter", as used interchangeably herein, mean the average diameter of the image of the particle as viewed by electron microscopy, unless otherwise stated. The size distribution of a collection of particles can be characterized by several values. The term "average particle size" and "average particle diameter" mean the number average of the particle sizes of a collection of particles.

The "span" for a distribution of particles can be computed from the formula $$\text{Span} = \frac{D_{v0.9} - D_{v0.1}}{D_{v0.5}};$$

where $D_{v0.1}$, $D_{v0.5}$, and $D_{v0.9}$ are defined such that 10%, 50%, and 90% of the particles in the collection of particles have a dimension smaller than $D_{v0.1}$, $D_{v0.5}$, and $D_{v0.9}$ respectively.

The coefficient of variation (COV) for a collection of particles is the standard deviation of particle sizes divided (normalized) by the average particle size.

The term "monodisperse", as used herein, characterizes a collection of particles where the particle size scatter is within a narrow range of sizes. A monodisperse collection of particles can be a collection of particles having a span of about 2 or less, about 1 or less, about 0.8 or less, or about 0.5 or less. A monodisperse collection of particles can be a collection of particles having a COV of about 0.5 or less, about 0.4 or less, or about 0.3 or less. A monodisperse collection of particles can be a collection of particles wherein about 40% or more, about 50% or more, about 60% or more, about 70% or more, or about 80% or more of the particles have a particle size within ±10 nm, ±8 nm, ±6 nm, ±5 nm, or ±3 nm of the average particle size for the collection of particles.

The terms "biocompatible" and "biologically compatible", as used interchangeably herein, refer to materials that are, with any metabolites or degradation products thereof, generally non-toxic to the recipient, and cause no significant adverse effects to the recipient. Generally, biocompatible materials are materials which elicit no significant inflammatory or immune response when administered to a patient. In some embodiments a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

The term "subject" refers to any individual who is the target of administration. The subject can be a vertebrate, for example, a mammal. The subject can be a human. The term denotes no particular age or sex. The term "patient" refers to a subject afflicted with a disease or disorder. The term "patient" includes human and veterinary subjects The terms "standard electrode potential" and "standard potential", as used interchangeably herein, refer to the potential (voltage) developed by a reversible electrode when the activities of all ions in the cell are unity, all gases are at 1 atm pressure, and all solids are in their most stable form at 25° C. The "standard electrode potential" can be reported as a reduction potential. The "standard electrode potential" of a species, $M^{n+}$, can be measured against the standard hydrogen electrode as the potential of the right-hand electrode less that of the left-hand electrode in the cell:

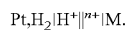

The "standard electrode potential" can be used as one measure of the oxidizing ability or strength of an oxidizing agent. Unless otherwise indicated, standard electrode potentials reported herein are reduction potentials and the larger (more positive) the standard electrode potential the stronger the oxidizing ability of the oxidizing agent Methods of Making Graphene Quantum Dots Methods of making graphene quantum dots (GQDs) are provided. The methods include combining a graphene source with a strong oxidizing mixture to form a combination; and heating the combination to an elevated temperature to produce the GQDs. The methods can be performed in a single-step, e.g. the methods can be performed without the need to produce graphene oxide. The graphene source can be carbon black, graphite, or a combination thereof. The elevated temperature can be can be about 100° C. or more, for example about 100° C. to 200° C., about 120° C. to 180° C., or about 140° C. to 160° C. In some embodiments the heating is for a period of time of about 5 hours, 4 hours, 3 hours, 2.5 hours, 2.0 hours, 1.5 hours, 1.0 hours, or less. In some embodiments the heating is for a period of time less than 2 hours, less than 1.5 hours, or less than 1 hour.

Strong Oxidizing Mixture

The methods can include combining the graphene source with a strong oxidizing mixture. The strong oxidizing mixture can include oxidizing agents such as permanganates, hexafluoromanganates, persulfates, chromates, Fenton's reagent, oxidizing acids, and combinations thereof. The strong oxidizing mixture can have a standard electrode potential or can contain at least one, two, three, or more oxidizing agents having a standard electrode potential wherein the standard electrode potential is about 0.5 V to 5 V, about 0.9 V to 3.0 V, about 1.0 V to 2.5 V, about 1.0 V to 2.0 V, about 1.0 V to 1.6 V, or about 1.2 V to 1.6 V. In some embodiments at least one, two, three, or more oxidizing agents have a standard electrode potential that is about 0.9 V, 1.0V, 1.1 V, 1.2 V, 1.3 V, 1.4 V, or greater and a standard electrode potential that is about 5.0 V, 4.0 V, 3.5 V, 3.0 V, 2.5 V, 2.0 V, or less.

The strong oxidizing mixture can include at least one, two, three, or more oxidizing agents selected from of permanganates, hexafluoromanganates, persulfates, and chromates. The strong oxidizing mixture can include at least one, two, three, or more strong oxidizing agents selected from a permanganate, a peroxydisulfate, a bromate, a perchlorate, a chlorate, manganese dioxide, nitrous oxide, and ozone. The permanganate can be potassium permanganate, ammonium permanganate, calcium permanganate, sodium permanganate, or silver permanganate.

The oxidizing mixture can include oxidizing agents such as permanganates, hexafluoromanganates, persulfates, chromates, Fenton's reagent, oxidizing acids, and combinations thereof. The permanganate can include sodium permanganate, potassium permanganate, or calcium permanganate. The persulfate can include sodium peroxomonosulfate, sodium persulfate, potassium peroxymonosulfate, or ammonium persulfate. Oxidizing acid can include nitric acid, perchloric acid, chloric acid, chromic acid, sulfuric acid, and combinations thereof. In some embodiments the oxidizing mixture contains three or more oxidizing agents. In some embodiments the oxidizing mixture contains at least two oxidizing acids. The oxidizing acids can include nitric acid, perchloric acid, chloric acid, chromic acid, and sulfuric acid.

In some embodiments the oxidizing mixture can contain a permanganate such as potassium permanganate, nitric acid, and sulfuric acid.

Graphene Quantum Dots

The methods can make small GQDs with a monodisperse size distribution. Graphene quantum dots (GQDs) are provided. The GQDs can be prepared by one of the methods described herein. The methods provide a plurality of GQDs having a small size and/or a monodisperse size distribution. Compositions are provided containing the plurality of GQDs. The GQDs can have an average diameter of about 1.0 nm to 20.0 nm, about 2.0 nm to 10.0 nm, or about 2.0-5.0 nm. The monodisperse size distribution can have a span of less than 1, e.g. about 1.0, 0.9, 0.8, 0.7 or less. The monodisperse size distribution can have a coefficient of variation of less than about 0.5, e.g. about 0.5, 0.4 0.3, 0.25 or less. In some embodiments, at least 40%, at least 50%, at least 60%, or at least 75% of the GQDs have a diameter within ±0.5 nm of the average diameter of the GQDs. The GQDs can have a lattice spacing of about 0.25 nm, 0.24 nm, 0.23 nm, 0.22 nm, or less.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Measurement of Quantum Yield of GQDs

Quinine sulfate in 0.1 M $H_2SO_4$ (QY=0.543) was chosen as standard. The quantum yields of GQDs (in water) were calculated according to:

$$\phi_x = \phi_{st}\left(\frac{I_x}{I_{st}}\right)\left(\frac{\eta_x^2}{\eta_{st}^2}\right)\left(\frac{A_{st}}{A_x}\right)$$

Where $\phi$ is the quantum yield, I is the measured integrated emission intensity, $\eta$ is the refractive index of the solvent, and A is the absorbance. The subscript "st" refers to standard with known quantum yield and "x" for the sample.

TABLE 1

Quantum yield of GQDs using quinine sulfate as a reference

| Sample | Integrated emission intensity(I) | Absorbance (A) | Refractive index of the solvent($\eta$) | Quantum yield($\phi$) |
|---|---|---|---|---|
| Quinine sulfate | 3432500 | 0.0668 | 1.33 | 0.543 |
| GQDs | 1207000 | 0.0971 | 1.33 | 0.131 |

Example 1

Preparation of GQDs

GQDs with green fluorescence were synthesized by a one-step chemical oxidation reaction directly from graphite powder. The exemplary synthesis is depicted in FIG. 1. This method takes little time, as fast as 90 minutes, with the photoluminescence quantum yield of 13.1% (quinine sulfate of 0.54 as the reference).

Figure 2:
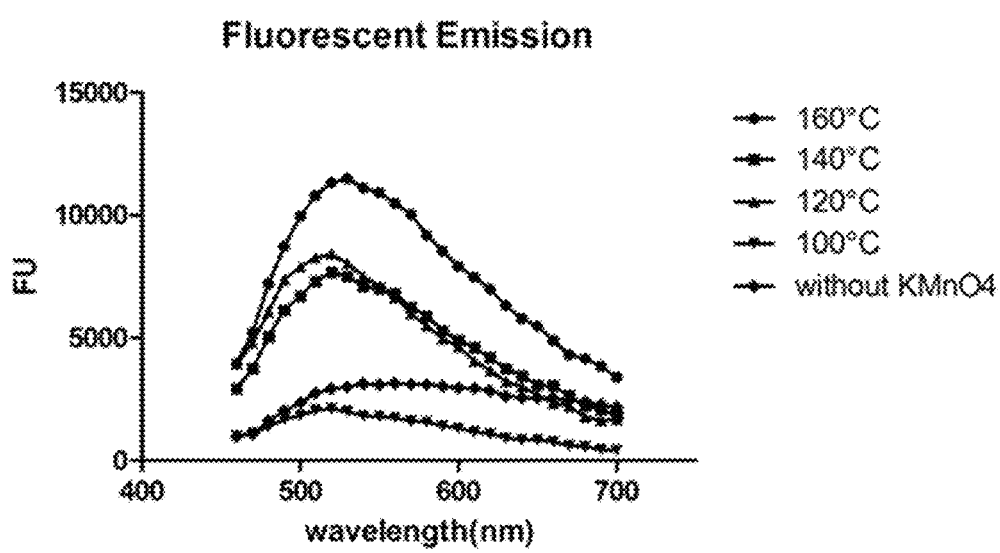
FIG. 2 is a graph of the fluorescence emission sprectra of graphene quantum dot production in the presence of $HNO_3$, $H_2SO_4$, and $KMnO_4$ as a function of temperature. The fluorescence emission spectra in the presence of $HNO_3$ and $H_2SO_4$ (without $KMnO_4$) is included as a reference.
Figure 3:
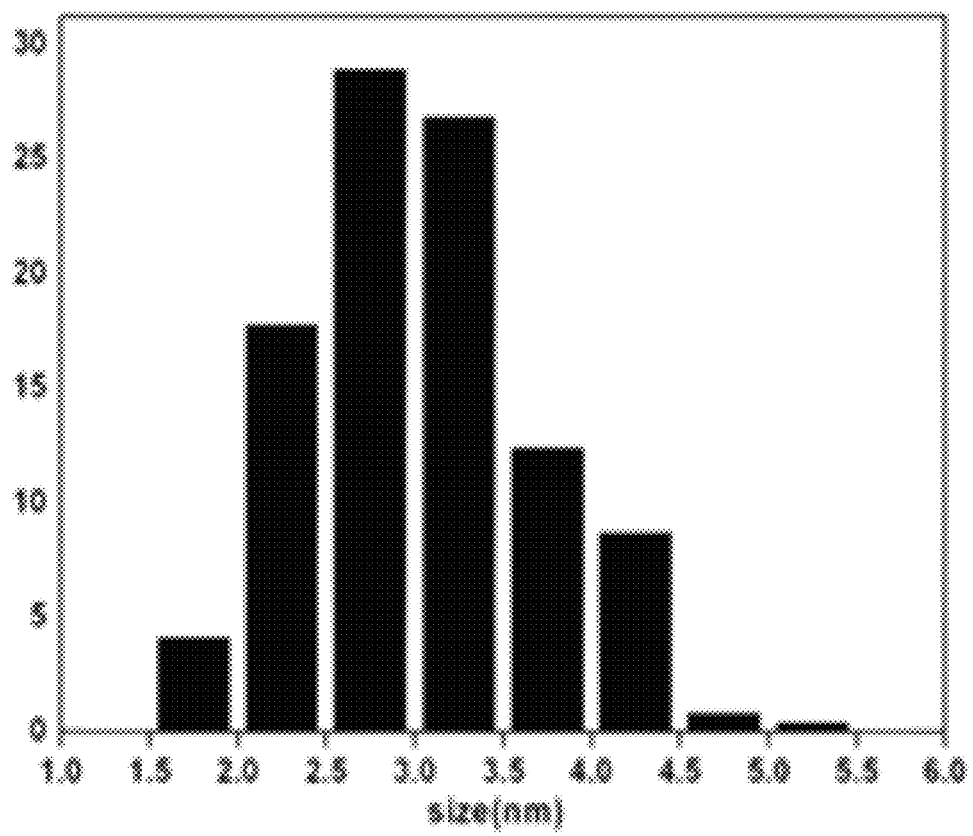
FIG. 3 is a bar graph of the size distribution (%, along the left axis) as a function of the graphene quantum dot diameter (nm, along the bottom axis) depicting the monodisperse size distribution of the graphene quantum dots.

The sizes of the GQDs were evaluated via Transmission Electron Microscopy image and size distribution of GQDs, depicted in FIG. 3, indicates a monodisperse size distribution that has a relatively narrow distribution between 1.5 to 5.5 nm with an average diameter of 3.03 nm. High-resolution TEM (HRTEM) image of the GQD and the corresponding (SAD) pattern indicated the high crystallinity of the GQDs with a lattice parameter of 0.21 nm. Topographic morphology of the GQDs was obtained from Atomic Force Microscope with an average height of about 1 nm. The AFM images demonstrated that most of the GQDs are single or bi-layered, suggesting that all the graphene sheets with multiple layers were tailored into small GQDs sheets by the synergistic interaction of $KMnO_4$, concentrated $H_2SO_4$, and $HNO_3$. To examine the role of these three oxidants, the reaction were carried out under the same conditions without $KMnO_4$, or $H_2SO_4$, and $HNO_3$. We carried out a series synthesis reactions at different temperature points and measure the PL behavior of as-synthesized GQDs. The results depicted in FIG. 2 demonstrate the formation of GQDs begins as the temperature is heated above 100° C. When the temperature is lower than 100° C. or without $KMnO_4$, the fluorescent emission significantly dropped down.

Figure 4:
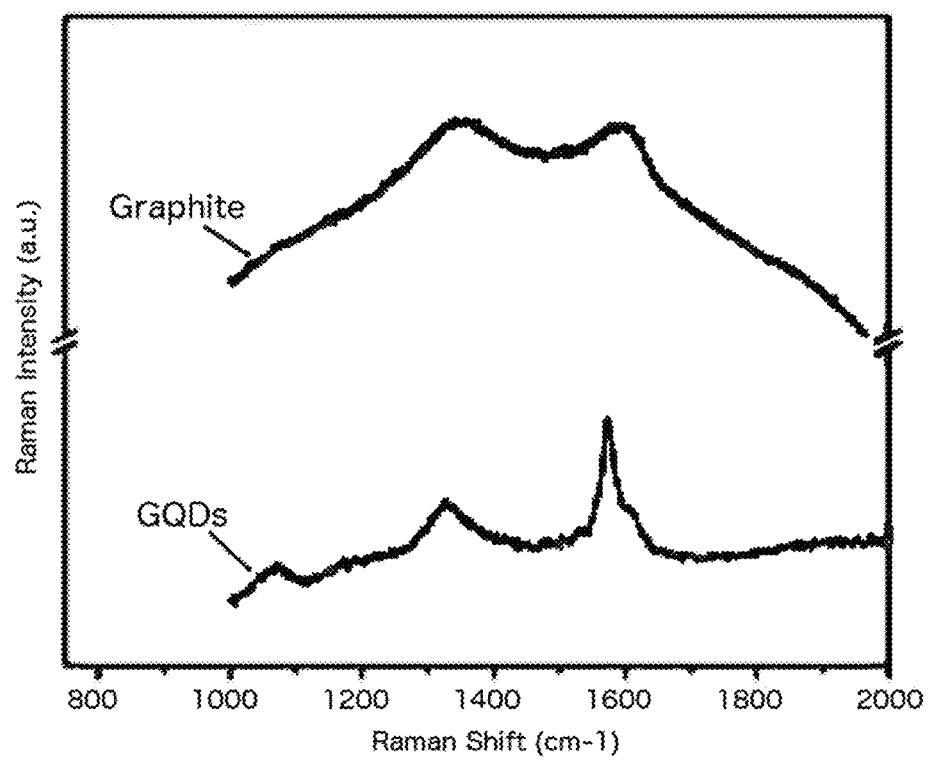
FIG. 4 is a graph of the Raman spectra of graphite (top) and the graphene quantum dots of Example 1 (bottom).
Figure 5:
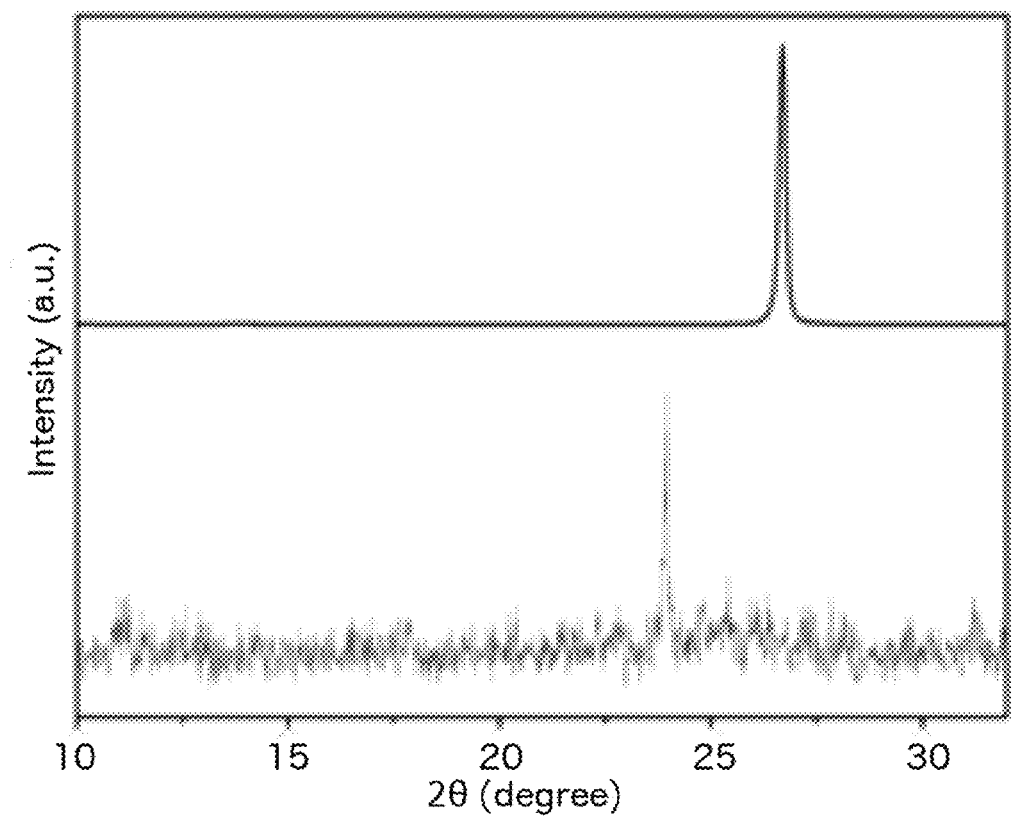
FIG. 5 is a graph of the X-ray diffraction pattern of graphite (top) and the graphene quantum dots of Example 1 (bottom).

Raman spectroscopy was also used to characterize the GQDs. As indicated in FIG. 4, the Raman spectra of GQDs is resolved into two distinctive D and G bands at ~1340 and ~1580 $cm^{-1}$, while that of graphite is at ~1328 and ~1572 $cm^{-1}$. In case of nanocrystalline graphite, the intensity ratio ($I_D/I_G$) is known to inversely proportional to the crystalline grains. This suggests that GQDs are more defective than graphene sheets, possibly due to the dominant contributions from the edge states at the periphery of GQDs. The typical XRD patterns of graphite and the GQDs are presented in FIG. 5. With graphite, its interlayer spacing is 0.335 nm, which is in accordance with previous reports. The interlayer spacing of GQDs, however, expand to 0.372 nm which is determined by Bragg's law $2d \sin \theta = n\lambda$, and a peak (002) centered at 23.87 degree is observed. In comparison with graphite, the XRD peaks for GQDs shifted to a lower degree, revealing a larger interlayer distance than the initial graphite. This is mainly ascribed to the oxygen-containing groups introduced in the exfoliation and oxidation of graphite, leading to the enhancement of interlayer spacing.

Figure 6:
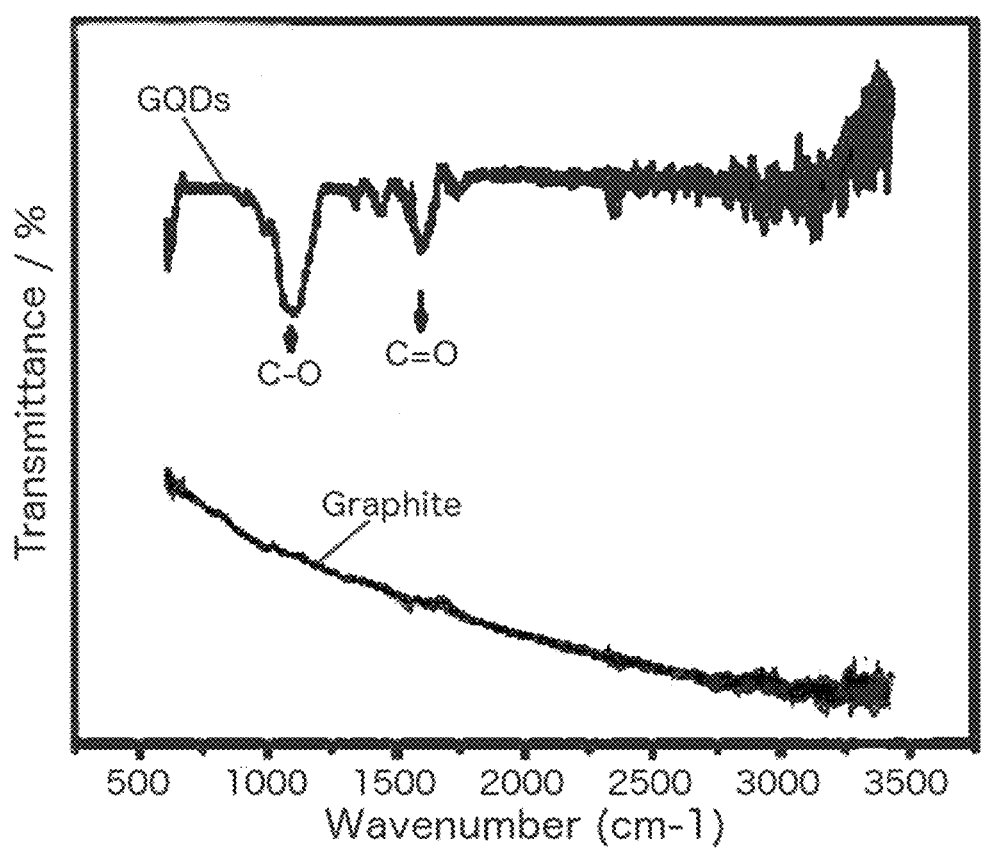
FIG. 6 is a Fourier Transmission Infrared (FTIR) spectrum of graphite (bottom) and the graphene quantum dots of Example 1 (top) depicting the presence of the C—O and C=O stretching modes in the graphene quantum dots.
Figure 7:
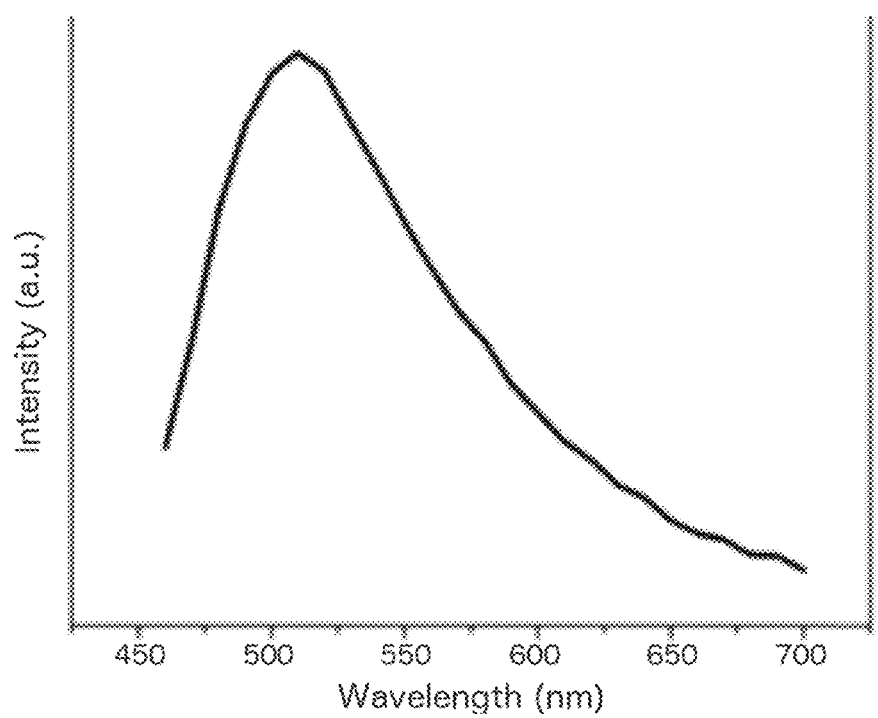
FIG. 7 is a graph of the fluorescence emission spectra of the graphene quantum dots of Example 1 (excited at 440 nm).

As the Fourier transform infrared (FTIR) spectrum in FIG. 6 showed, many chemical groups such as C—O, C=O, were introduced to the edges of GQDs during the oxidation cutting process, which makes GQDs possess excellent solubility in water, PBS, cell culture medium, and many organic solvents. FIG. 7 shows the photoluminescence spectra of GQDs aqueous solution at 440 nm excitation. Like most luminescent carbon nanoparticles, the GQDs also exhibit an excitation-dependent PL behavior. To explore the optical properties of the GQDs, we carried out a detailed PL study by using different excitation wavelengths. The emission peaks of GQDs shift with varying excitation, exhibiting excitation-dependent PL behavior.

Figure 8:
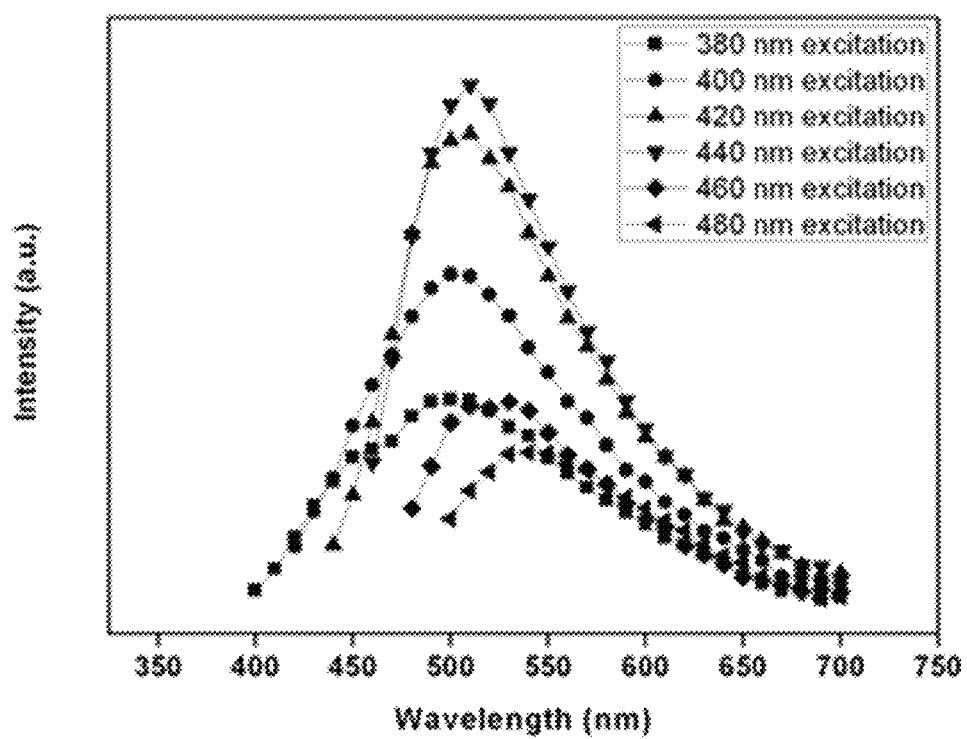
FIG. 8 is a graph of the fluorescence emission spectra of the graphene quantum dots of Example 1 as a function of the excitation wavelength.
Figure 9:
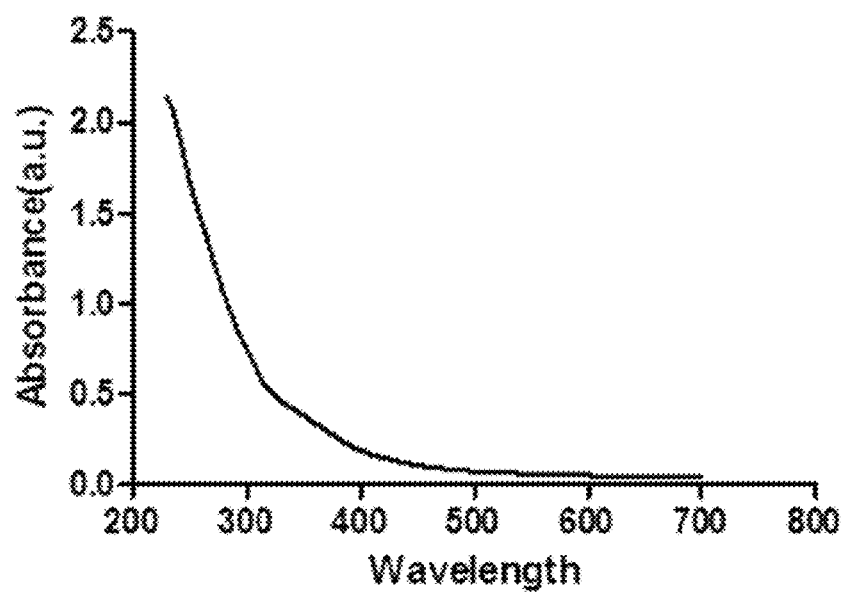
FIG. 9 is a graph of the UV-VIS absorption spectrum of the graphene quantum dots of Example 1.

The emission peak will shift when change the excitation wavelength (As in FIG. 8). Inset is the photograph of GQDs aqueous solution taken under 365 nm UV light which green fluorescence is visible by naked eye. The UV-visible absorption spectrum is shown as FIG. S3. At 230 nm, there is a strong absorption peak of $\pi \rightarrow \pi^*$ transition of aromatic sp2 domains. Besides, a new absorption shoulder around 350 nm can be observed, which is similar to other groups' work.

Example 2

Cytotoxity of GQDs

The fluorescence of GQDs prepared in Example 1 was measured in vitro is by confocal microscopy. A choriocarcinoma cancer cell line Jar was incubated with GQDs of Example 1 for 4 hours. The green fluorescence of GQDs was observed in cytosol as compared with the red fluorescence of DRAQ5. Fluorescence microscopy images indicated the GQDs were stable and localized in the cystol.

Figure 10:
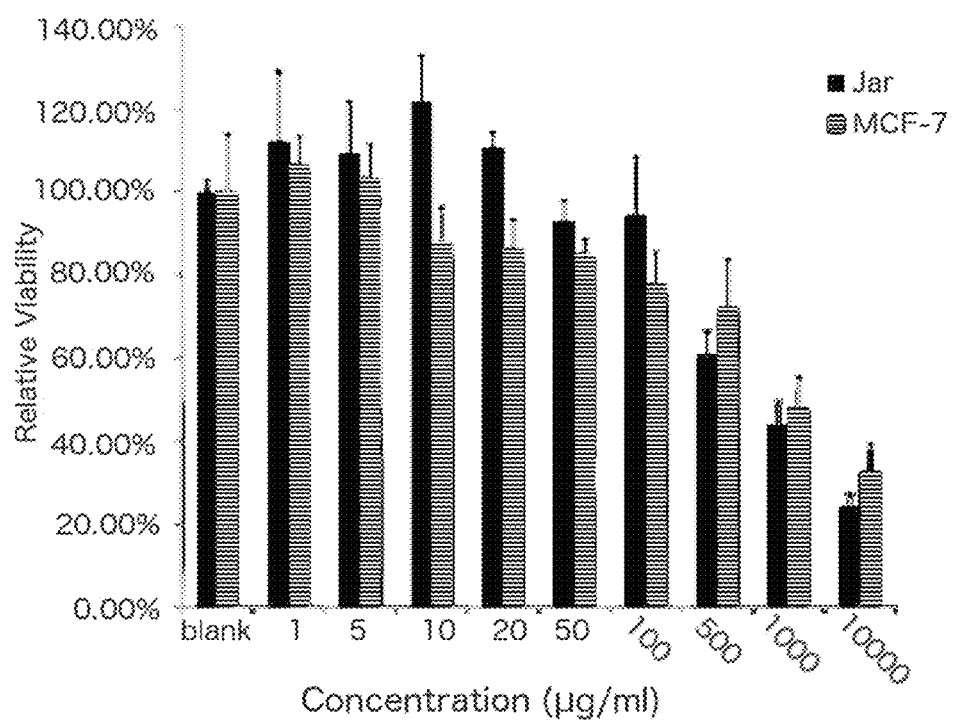
FIG. 10 is a bar graph of the relative cellular viability (% viability) along the left axis as a function of the concentration (μg/ml) of the graphene quantum dots for Jar cells and for MCF-7 cells. For each concentration along the bottom axis the left bar is the relative viability for the Jar cells and the right bar is the relative viability for the MCF-7 cells.

To test the cytotoxicity of GQDs, the choriocarcinoma cancer cell line Jar and breast cancer cell line MCF-7 was incubated for 24 hours with different concentrations of GQDs from Example 1. The results in FIG. 10 demonstrate the cells remained viable at concentration up to at least 100 μg/ml. Up to a GQD concentration of 100 μg/ml, the relative viability of Jar cells is higher than 90% and the relative viability of MCF-7 cells is higher than 80%, demonstrating that GQDs possess relatively low cytotoxicity and high biocompatibility.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are included within this disclosure.

We claim:

1. A method of making graphene quantum dots (GQDs) comprising:
    combining a graphene source with a strong oxidizing mixture to form a combination; and
    heating the combination to an elevated temperature with respect to room temperature to produce the GQDs,
    wherein the strong oxidizing mixture comprises an oxidizing agent selected from the group consisting of a permanganate, a hexafluoromanganate, a persulfate, a chromate, Fenton's reagent, an oxidizing acid, and a combination thereof.

2. The method of claim 1, wherein the graphene source is selected from the group consisting of graphite, carbon black, and combinations thereof.

3. The method of claim 1, wherein the oxidizing mixture comprises a permanganate selected from the group consisting of potassium permanganate, ammonium permanganate, calcium permanganate, sodium permanganate, and silver permanganate.

4. The method of claim 1, wherein the strong oxidizing mixture comprises a persulfate selected from the group consisting of sodium peroxomonosulfate, sodium persulfate, potassium peroxymonosulfate, and ammonium persulfate.

5. The method of claim 1, wherein the strong oxidizing mixture comprises an oxidizing acid selected from the group consisting of nitric acid, perchloric acid, chloric acid, chromic acid, and sulfuric acid.

6. The method of claim 1, wherein the oxidizing mixture comprises three or more oxidizing agents.

7. The method of claim 1, wherein the oxidizing mixture comprises at least one permanganate and at least one oxidizing acid.

8. The method of claim 1, wherein the oxidizing mixture comprises potassium permanganate, nitric acid, and sulfuric acid.

9. The method of claim 1, wherein the elevated temperature is 100° C. to 200° C.

10. The method of claim 1, wherein the GQDs have an average diameter of between 2.0 nm and 10.0 nm.

11. The method of claim 1, wherein the GQDs have a monodisperse particle distribution.

12. The method of claim 1, wherein the heating is for a period of time of 2 hours or less.

13. The method of claim 1, wherein the strong oxidizing mixture comprises one or more oxidizing agents having a standard electrode potential between 1.0 V and 2.5 V.

14. A method of making graphene quantum dots (GQDs) comprising:
    combining a graphene source with a strong oxidizing mixture to form a combination; and
    heating the combination to an elevated temperature with respect to room temperature to produce the GQDs,
    wherein the oxidizing mixture comprises three or more oxidizing agents.

15. The method of claim 14, wherein the graphene source is selected from the group consisting of graphite, carbon black, and combinations thereof.

16. The method of claim 14, wherein the oxidizing mixture comprises a permanganate selected from the group consisting of potassium permanganate, ammonium permanganate, calcium permanganate, sodium permanganate, and silver permanganate.

17. The method of claim 14, wherein the strong oxidizing mixture comprises a persulfate selected from the group consisting of sodium peroxomonosulfate, sodium persulfate, potassium peroxymonosulfate, and ammonium persulfate.

18. The method of claim 14, wherein the strong oxidizing mixture comprises an oxidizing acid selected from the group consisting of nitric acid, perchloric acid, chloric acid, chromic acid, and sulfuric acid.

19. The method of claim 14, wherein the oxidizing mixture comprises at least one permanganate and at least one oxidizing acid.

20. The method of claim 14, wherein the oxidizing mixture comprises potassium permanganate, nitric acid, and sulfuric acid.

21. The method of claim 14, wherein the elevated temperature is 100° C. to 200° C.

22. The method of claim 14, wherein the GQDs have an average diameter of between 2.0 nm and 10.0 nm.

23. The method of claim 14, wherein the GQDs have a monodisperse particle distribution.

24. The method of claim 14, wherein the heating is for a period of time of 2 hours or less.

25. The method of claim 14, wherein the strong oxidizing mixture comprises one or more oxidizing agents having a standard electrode potential between 1.0 V and 2.5 V.

* * * * *